United States Patent
Charles

(10) Patent No.: US 11,672,612 B2
(45) Date of Patent: Jun. 13, 2023

(54) OPTICAL COHERENCE TOMOGRAPHY GUIDED ROBOTIC OPHTHALMIC PROCEDURES

(71) Applicant: Alcon Inc., Fribourg (CH)

(72) Inventor: Steven T. Charles, Memphis, TN (US)

(73) Assignee: Alcon Inc., Fribourg (CH)

( * ) Notice: Subject to any disclaimer, the term of this patent is extended or adjusted under 35 U.S.C. 154(b) by 108 days.

(21) Appl. No.: 17/408,533

(22) Filed: Aug. 23, 2021

(65) Prior Publication Data
US 2022/0061923 A1 Mar. 3, 2022

Related U.S. Application Data

(60) Provisional application No. 63/071,716, filed on Aug. 28, 2020.

(51) Int. Cl.
*A61B 34/20* (2016.01)
*A61B 34/30* (2016.01)
*G06T 7/70* (2017.01)
*A61B 3/10* (2006.01)

(52) U.S. Cl.
CPC .............. *A61B 34/20* (2016.02); *A61B 3/102* (2013.01); *A61B 34/30* (2016.02); *G06T 7/70* (2017.01); *A61B 2034/2051* (2016.02); *A61B 2034/2055* (2016.02); *G06T 2207/10101* (2013.01); *G06T 2207/30041* (2013.01)

(58) Field of Classification Search
CPC ......... A61B 34/20; A61B 3/102; A61B 34/30; A61B 2034/2051; A61B 2034/2055; A61B 2034/302; A61B 34/32; A61B 2034/2059; A61B 2090/3735; G06T 7/70; G06T 2207/10101; G06T 2207/30041; A61F 9/00736
See application file for complete search history.

(56) References Cited

U.S. PATENT DOCUMENTS

| | | | |
|---|---|---|---|
| 8,508,726 B2 | 8/2013 | Benner, Jr. |
| 9,649,021 B1 | 5/2017 | Charles |
| 10,013,749 B2 | 7/2018 | Charles |
| 10,064,549 B2 | 9/2018 | Charles |
| 10,285,584 B2 | 5/2019 | Charles |
| 10,398,307 B2 | 9/2019 | Charles |
| 10,634,523 B2 | 4/2020 | Guggenmos et al. |

(Continued)

*Primary Examiner* — Patricia J Park
*Assistant Examiner* — Adil Partap S Virk

(57) ABSTRACT

The systems and methods described herein provide improved techniques for OCT guided robotic ophthalmic procedures. A method includes receiving, during OCT scanning of an eye, position data of a plurality of galvanometer scanners from a plurality of absolute and incremental encoders coupled to the corresponding galvanometer scanners. The method further includes receiving scan data related to one or more tissues of the eye. The method further includes determining, a set of first positions of the one or more tissues of the eye in a first 3D coordinate system. The method further includes determining, based on the set of first positions and a mapping between the first and a second 3D coordinate systems, a position in the second 3D coordinate system for a surgical instrument coupled to a robotic device. The method includes causing the robotic device to move the surgical instrument to the position in the second 3D coordinate system.

15 Claims, 3 Drawing Sheets

(56) References Cited

U.S. PATENT DOCUMENTS

| | | | |
|---|---|---|---|
| 2007/0165134 A1* | 7/2007 | Hama | H04N 23/56 |
| | | | 348/370 |
| 2008/0042051 A1* | 2/2008 | Sidor | G01D 5/3473 |
| | | | 250/231.14 |
| 2015/0318011 A1* | 11/2015 | Onoe | G11B 7/0065 |
| | | | 369/44.32 |
| 2015/0335480 A1 | 11/2015 | Alvarez et al. | |
| 2017/0196460 A1* | 7/2017 | Kakuma | G01B 9/02091 |
| 2020/0124446 A1 | 4/2020 | Benner, Jr. et al. | |
| 2022/0361743 A1* | 11/2022 | Chan | A61B 1/018 |

\* cited by examiner

OPTICAL COHERENCE TOMOGRAPHY GUIDED ROBOTIC OPHTHALMIC PROCEDURES

BACKGROUND

Field

Embodiments of the present disclosure generally relate to methods and apparatus for ophthalmic procedures, and more particularly, to methods and apparatus for optical coherence tomography (OCT) guided robotic ophthalmic procedures.

Description of the Related Art

OCT guided robotic ophthalmic procedures may improve patient care. For example, OCT guided robotic vitreoretinal surgery may result in precise incisions of concerned tissues of a patient's eye, a more consistent operating procedure, and prevent human errors during the surgical procedure. In order to have a true OCT guided robotic ophthalmic procedure performed safely, the robotic device must be provided with accurate data of the locations of various tissues of the eye.

Existing OCT systems may be configured to perform OCT scans of an eye and detect various tissues of the eye. Existing OCT systems can be sensitive to heat generated from galvanometer scanners' heating due to $I^2R$ losses while OCT scanning is performed. Such heat may result in thermal drift of one or more components (e.g., galvanometer scanners, analog capacitive angle sensors, and the like) of the existing OCT systems. The thermal drift can cause the one or more scanning components of the OCT system to drift from an expected position. Similarly, friction caused by bearings of some moving components of some of the existing OCT systems may also result in thermal drift causing one or more components of the OCT system to drift from expected positions.

Generally, the thermal drift can result in angular position errors for the galvanometer scanners of the OCT system because the galvanometer scanners are limited-angle rotary actuators. The angular position errors may result in translation errors that can cause a system to erroneously target a tissue in the eye that can be up to 100 microns of distance away from a tissue plane selected by a user. Additionally, the analog capacitive angle sensors coupled to the galvanometer scanners are incapable of correcting for such thermal drift and to nullify an error in the range of 100 microns.

Therefore, certain existing OCT systems are incapable of accurately determining a position and orientation in space of a tissue in an eye being scanned by the OCT systems. Thus, such existing OCT systems cannot accurately guide robotic ophthalmic procedures.

SUMMARY

The present disclosure generally relates to methods and apparatus for OCT guided robotic ophthalmic procedures.

In certain embodiments, an optical coherence tomography (OCT) system includes a plurality of galvanometer scanners, a plurality of absolute encoders, and a plurality of incremental encoders, each one of the plurality of absolute encoders and each one of the plurality of incremental encoders coupled to at least one of the plurality of galvanometer scanners. The OCT system further includes a controller coupled to the plurality of absolute encoders and the plurality of incremental encoders. The controller includes a processor, and a memory coupled to the processor and having instructions stored thereon, which when executed by the processor, causes the controller to receive, during an optical coherence tomography (OCT) scanning of an eye, position data of the plurality of galvanometer scanners from the plurality of absolute encoders and the plurality of incremental encoders coupled to the corresponding galvanometer scanners. The processor also causes the controller to receive, during the OCT scanning, scan data related to one or more tissues of the eye. The processor also causes the controller to determine, based on the received position data and the scan data, a set of first positions of the one or more tissues of the eye in a first three-dimensional (3D) coordinate system. The processor also causes the controller to determine, based on the first set of positions and a mapping between the first 3D coordinate system and a second 3D coordinate system, a position in the second 3D coordinate system for a surgical instrument coupled to a robotic device. The processor also causes the controller to cause the robotic device to move the surgical instrument to the position in the second 3D coordinate system.

In certain embodiments, a method generally includes receiving, during an optical coherence tomography (OCT) scanning of an eye, position data of a plurality of galvanometer scanners from a plurality of absolute encoders and a plurality of incremental encoders coupled to the corresponding galvanometer scanners, each one of the plurality of absolute encoders and each one of the plurality of incremental encoders coupled to at least one of the plurality of galvanometer scanners. The method further includes receiving, during the OCT scanning, scan data related to one or more tissues of the eye. The method further includes determining, based on the received position data and the scan data, a set of first positions of the one or more tissues of the eye in a first three-dimensional (3D) coordinate system. The method further includes determining, based on the first set of positions and a mapping between the first 3D coordinate system and a second 3D coordinate system, a position in the second 3D coordinate system for a surgical instrument coupled to a robotic device. The method further includes determining, based on the first set of positions and a mapping between the first 3D coordinate system and a second 3D coordinate system, a position in the second 3D coordinate system for a surgical instrument coupled to a robotic device.

Aspects of the present disclosure provide means for, apparatus, processors, and computer-readable mediums for performing the methods described herein.

BRIEF DESCRIPTION OF THE DRAWINGS

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrate only exemplary embodiments and are therefore not to be considered limiting of its scope, and may admit to other equally effective embodiments.

To facilitate understanding, identical reference numerals have been used, where possible, to designate identical elements that are common to the figures. It is contemplated that elements and features of one embodiment may be beneficially incorporated in other embodiments without further recitation.

DETAILED DESCRIPTION

The present disclosure generally relates to methods and apparatus for OCT guided robotic ophthalmic procedures.

As described herein, a robotic ophthalmic procedure may be an ophthalmic procedure that is performed by a robotic device based on user input received from a user. The user input may include a selection of the ophthalmic procedure, selection of a target tissue, an instruction to perform the selected procedure, etc.

Existing OCT systems may be configured to scan an eye and a surgeon may identify one or more tissues of the eye on an image generated based on the scan data from the scan of the eye combined with stereo digital visualization. However, existing OCT systems are generally not configured to provide accurate positions or locations of the one or more tissues of an eye. For example, OCT systems are generally configured with galvanometer scanners that are coupled to analog capacitance angle sensors. However, heat generated from some components (e.g., galvanometer scanners) of an OCT system and/or bearing friction from movements of an OCT system's components can result in thermal drift that can cause angular errors when determining angular positions of the galvanometer scanners of the OCT system. Such thermal drift can result in a translational error generally in the range of 100 microns when determining a position of a tissue in an eye. While such thermal drift may have minimal effect on OCT image generation, it can be dangerous to try to determine positions and/or locations of the various tissues of the eye in a coordinate system without correcting for and/or eliminating the thermal drift. Therefore, existing OCT systems are not capable of accurately guiding robotic ophthalmic procedures.

Accordingly, some implementations of the present disclosure provide various systems and techniques that improve an OCT system's accuracy in determining a position of one or more tissues in an eye and effectively guiding a robotic device to move a surgical instrument to a tissue in the eye. Some implementations of the present disclosure provide various systems and techniques to configure an OCT system to receive inputs related to one or more target tissues of a scanned eye from a user (e.g., a surgeon, and the like), and configure the OCT system to determine the positions or locations of the one or more target tissues of the eye in a coordinate system of the OCT system. Some implementations of the present disclosure provide various systems and techniques to configure the OCT system to provide to the robotic device, positions or locations of the one or more target tissues of the eye in a coordinate system of the robotic device, and cause the robotic device to move a surgical or another medical instrument coupled to the robotic device to the one or more target tissues based on the provided positions or locations.

Figure 1A:
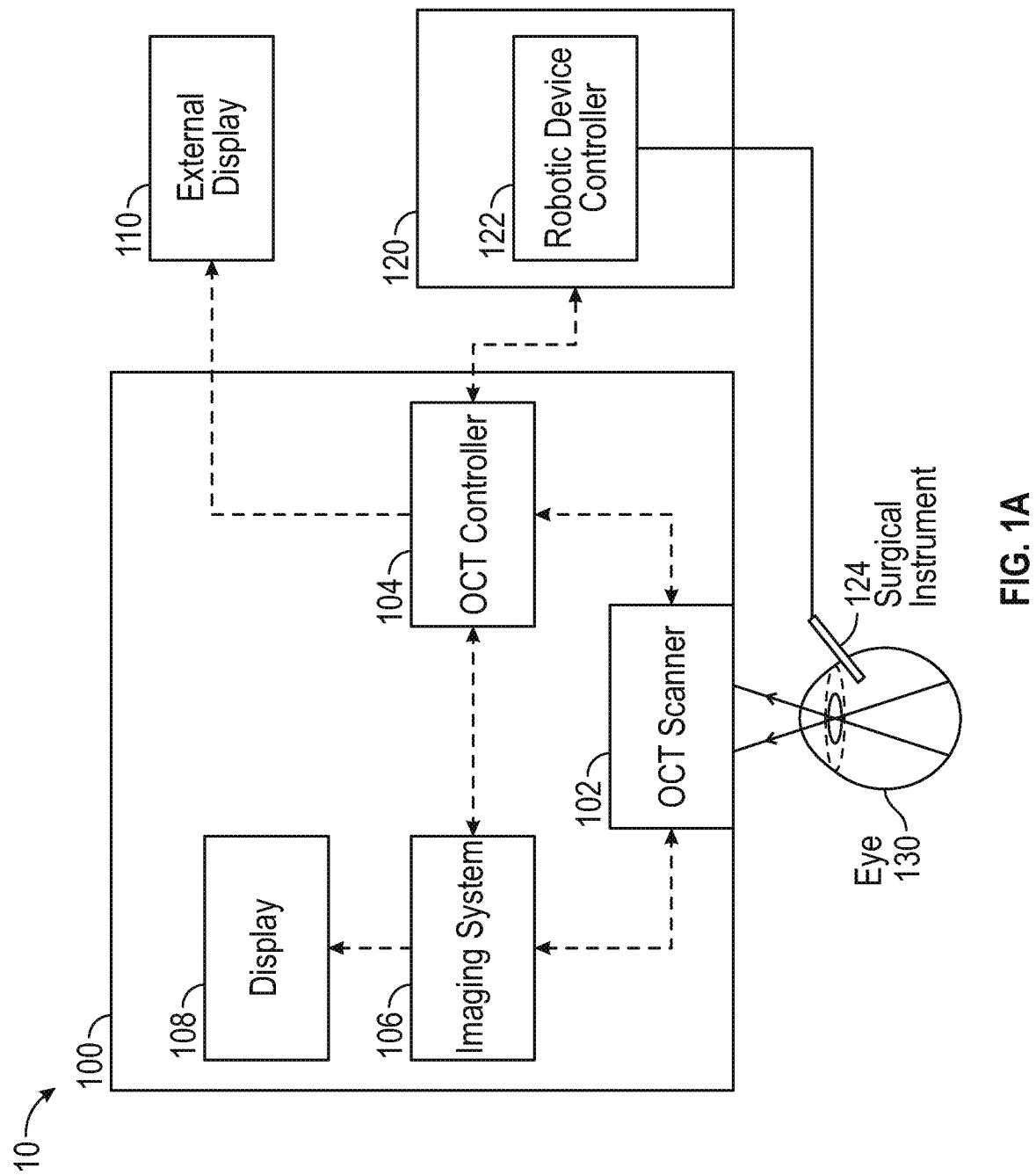
FIG. 1A illustrates a block diagram of selected components of an example OCT guided robotic ophthalmic surgical system, in accordance with certain embodiments of the present disclosure.

FIG. 1A illustrates a block diagram of selected components of an example optical coherence tomography (OCT) guided robotic ophthalmic surgical system 10. The OCT guided robotic ophthalmic surgical system 10 includes an OCT system 100 and a robotic device 120. The OCT system 100 includes an OCT scanner 102, an OCT controller 104, an imaging system 106, and a display 108. The OCT system 100 may be communicatively coupled to the robotic device 120 and an external display 110.

The OCT scanner 102 may include a number of OCT components and/or instruments (not shown separately in FIG. 1A). The OCT components and/or instruments may be of various types, and the OCT scanner 102 may be configured differently based on the types of the OCT components and/or instruments. The OCT scanner 102 performs OCT scanning of an eye 130 of a patient. The OCT scanner 102 may perform the OCT scanning by controlling output of one or more sample beams (not shown) onto the eye 130, and receiving one or more measurement beams (not shown) reflected back from the eye 130. The one or more measurement beams may be reflected back from the eye 130 in response to the photons of the sample beam interacting with the tissue in the eye 130. In some implementations, the OCT scanner 102 may be configured as a time domain OCT (TD-OCT). In some implementations, the OCT scanner 102 may be configured as a frequency domain OCT (FD-OCT). In some implementations, the OCT scanner 102 may be configured as a swept-source OCT (SS-OCT).

The OCT scanner 102 may include multiple galvanometer scanners (not shown separately in FIG. 1A), and may control the output of one or more sample beams onto the eye 130 using the galvanometer scanners. In some implementations, the OCT scanner 102 may include dual galvanometer scanners. Each galvanometer scanner of the OCT scanner 102 may be configured to scan in a certain direction. For example, one galvanometer scanner of the OCT scanner 102 may be configured to scan in a first direction, and another galvanometer scanner of the OCT scanner 102 may be configured to scan in a second direction. In some implementations, the first direction and the second direction may be different directions. In some implementations, the first direction may be perpendicular to the second direction. In some implementations, one galvanometer scanner of the OCT scanner 102 may scan in a first direction on a first scan plane, and another galvanometer scanner of the OCT scanner 102 may scan in a second direction on a second scan plane. In some implementations, the first scan plane may be perpendicular to the second scan plane.

Each galvanometer scanner may be coupled to an absolute encoder (not shown separately in FIG. 1A) and an incremental encoder (not shown separately in FIG. 1A). For example, if the OCT scanner 102 includes two galvanometer scanners, then a first absolute encoder and a first incremental encoder may be coupled to the first galvanometer scanner, and a second absolute encoder and a second incremental encoder may be coupled to the second galvanometer scanner. In some implementations, the absolute encoders coupled to the galvanometer scanners of the OCT scanner 102 may be optical rotary absolute encoders. In some implementations, the incremental encoders coupled to the galvanometer scanners of the OCT scanner 102 may be optical rotary incremental encoders. In some implementations, an absolute encoder and an incremental encoder may be coupled to a shaft connected to one or more elements (e.g., a mirror) of a galvanometer scanner. The absolute encoder may be configured to measure an absolute or true angular position of the galvanometer scanner based on the rotation of the shaft connected to an element (e.g., mirror) of the galvanometer scanner. The incremental encoder may be configured to measure a change in the angular position of the galvanometer scanner based on the rotation of the shaft connected to an element (e.g., mirror) of the galvanometer scanner.

The absolute encoders coupled to the galvanometer scanners of the OCT scanner 102 may be configured to determine the absolute or true angular positions of the corresponding galvanometer scanners without a performing a homing process to initialize or reinitialize after any power interruptions or thermal drift. The absolute encoders and the incremental encoders coupled to the galvanometer scanners of the OCT scanner 102 may be configured to have high angular resolution. The incremental encoders coupled to the galvanometer scanners of the OCT scanner 102 may be configured to have higher angular resolution than the absolute encoders coupled to the galvanometer scanners of the OCT scanner 102. Therefore, utilizing a combination of an absolute encoder and an incremental encoder is advantageous because the absolute encoder can provide the absolute or true angular position of a galvanometer scanner to a controller, such as the OCT controller 104, without performing a homing a process after any thermal drift or power interruptions, and the incremental encoders, with the higher angular resolution, can accurately detect even small changes in the angular positions of the galvanometer scanner and accurately track changes in the galvanometer scanner's angular position. In some implementations, the absolute encoders and the incremental encoders coupled to the galvanometer scanners of the OCT scanner 102 may measure resolution values in bits resolution, e.g., typically 16 bits resolution or more.

Each absolute encoder may be configured to generate an output including a unique configuration of bits for each position of the galvanometer scanner to which the absolute encoder is coupled. The unique configuration of bits generated by the absolute encoder indicates position data of the corresponding galvanometer scanner to which the absolute encoder is coupled. In some implementations, the output of each incremental encoder is analog proportional to the sine-cosine of the scan angle. The output of the incremental encoder indicates the position of the galvanometer scanner to which the incremental encoder is coupled.

Each absolute and incremental encoder included in the OCT scanner 102 may capture angular position data of the corresponding galvanometer scanner to which the absolute and the incremental encoder are coupled and transmit the position data to the OCT controller 104. In some implementations, the absolute incremental encoders may be configured to transmit the position data to the OCT controller 104 in real-time and/or near real-time. In some implementations, one absolute encoder and one incremental encoder may be integrated into a single encoder device. Additional details of the absolute and incremental encoders is described below with reference to FIG. 1B.

The position data of the corresponding galvanometer scanner may indicate a position of a mirror of the galvanometer scanner during an OCT scan of a patient's eye (e.g., eye 130). For example, position data from the absolute encoder coupled to a galvanometer scanner, configured to scan in a first direction on a first scan plane, may indicate positions of the mirror of the galvanometer scanner rotating in the first direction on the first scan plane during the OCT scanning of the eye 130. Similarly, position data from the absolute encoder coupled to a galvanometer scanner, configured to scan in a second direction on a second scan plane, may indicate positions of the mirror of the galvanometer scanner rotating in the second direction on the second scan plane during the OCT scan of the eye 130. As described above, in some implementations, the first scan plane may be perpendicular to the second scan plane. As described above, in some implementations, the first direction may be different from the second direction. As described above, in some implementations, the first and the second direction may be in the same direction.

Figure 1B:
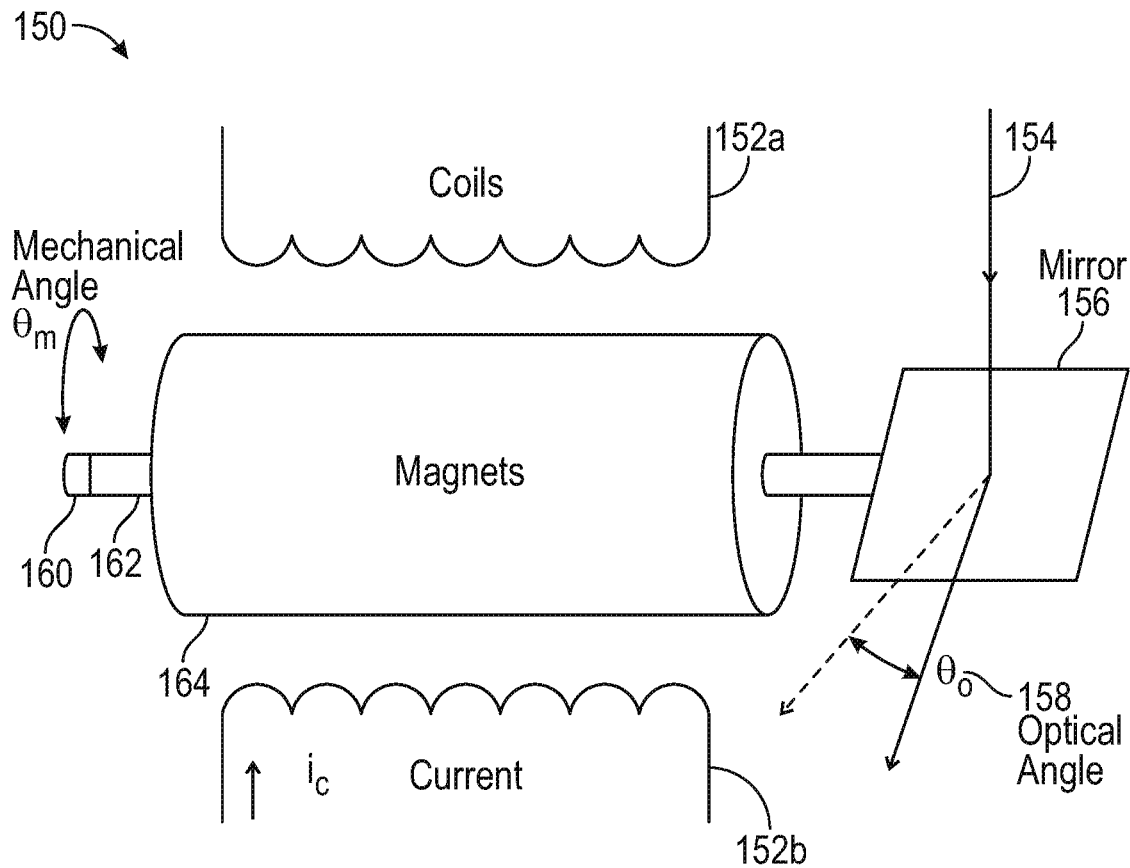
FIG. 1B illustrates a perspective view of a galvanometer scanner, in accordance with certain embodiments of the present disclosure.

An example of a galvanometer scanner is shown in FIG. 1B. The galvanometer scanner shown in FIG. 1B is a moving-magnet galvanometer scanner. FIG. 1B illustrates a perspective view of a galvanometer scanner 150. The galvanometer scanner 150 may include a mirror 156 and one or more magnets 164. The mirror 156 and the one or more magnets 164 may be connected to each other via a shaft 162. In some implementations, the shaft 162 may be a steel shaft. The galvanometer scanner 150 may include coils 152*a*-152*b*. The coils 152*a*-152*b* may surround the one or more magnets 164 as shown in FIG. 1B.

An encoder device 160 may include an absolute encoder and an incremental encoder, and the encoder device 160 may be coupled to the galvanometer scanner 150. For example, as shown in FIG. 1B, the encoder device 160 may be connected to the mirror 156 and the one or more magnets 164 via shaft 162. During the OCT scanning of the eye of the patient, the mirror 156 may rotate in response to the Lorentz force induced by coil current $l_c$ with the one or more magnets 164. As the mirror 156 rotates, the different angular positions of the mirror 156 are captured and/or measured by the encoder device 160. The angular position of the mirror 156 may be referred to herein as a mechanical angle of the mirror 156. The absolute encoder of the encoder device 160 may be configured to generate a unique configuration of bits for each angular position or mechanical angle of the mirror 156. The incremental encoder of the encoder device 160 may be configured to track the change in angular positions or mechanical angles of the mirror 156 as the mirror 156 rotates. As described above, the mechanical angles of a mirror of a galvanometer scanner during an OCT scan may indicate positions of the galvanometer scanner as described herein. Therefore, the various captured and/or measured mechanical angles of the mirror 156 during the OCT scan indicate the various positions of the galvanometer scanner during the OCT scan The encoder device 160 may transmit the outputs of the absolute incremental encoders as the position of the galvanometer scanner 150 to the OCT controller 104. As described above, in certain implementations, the outputs of the absolute and incremental encoders may indicate or be referred to herein as the position data of a galvanometer scanner (e.g., galvanometer scanner 150) to which the absolute encoder and the incremental encoder are coupled. During the OCT scanning, the encoder device 160 may transmit the outputs of the absolute encoder and the incremental encoder to the OCT controller 104.

In some implementations, the absolute encoder of the encoder device 160 may be a sine-cosine encoder. In some implementations, the absolute encoder of the encoder device 160 may be a holographic encoder. In some implementations, the absolute encoder of the encoder device 160 may have a grating and/or a holographic optic element (not shown separately) mounted on the absolute encoder of the encoder device 160. In certain implementations, the incremental encoder that operates with the absolute encoder of the encoder device 160 is holographic.

During the OCT scanning, one or more sample beams 154 may be directed at mirror 156. As the mirror 156 rotates during the OCT scanning, the rotations in the mirror 156 may change the angle of deflection of the one or more sample beams 154. The angle of deflection of the one or more sample beams 154 may be referred to herein as an optical angle of the one or more sample beams 154. In some implementations, the OCT scanner 102 may transmit the different optical angles of the one or more sample beams 154 as part of and/or along with the scan data transmitted to the OCT controller 104.

Returning to FIG. 1A, the OCT scanner 102 may be configured to scan the eye 130 at various depths of the eye 130. For example, the OCT scanner 102 may be configured to scan the entire depth of the eye 130 for a full eye scan of the eye 130. Similarly, the OCT scanner 102 may be configured to scan any portion of the eye 130, such as the retina of the eye 130. In some implementations, the OCT scanner 102 may scan different depths of the eye 130 at different resolutions. For example, the OCT scanner 102 may scan the entire depth of the eye 130 at a lower resolution, and may scan a portion of the eye 130, such as the retina of the eye 130, at a higher resolution.

The OCT scanner 102 may be configured to generate scan data based on the one or more measurement beams reflected back from the eye. The scan data may represent a depth profile of the scanned tissue. In some implementations, the scan data generated by the OCT scanner 102 may include two-dimensional (2D) scan data of a line scan (B-scan). In some implementations, the scan data generated by the OCT scanner 102 may include three-dimensional (3D) scan data of an area scan (C-scan, en face). The OCT scanner 102 may be configured to transmit the generated scan data to the OCT controller 104. In some implementations, the OCT scanner 102 may be configured to transmit the generated scan data in real-time or near real-time. In some implementations, the OCT scanner 102 may be configured to transmit the generated scan data after the entire scanning operation is completed by the OCT scanner 102.

The OCT scanner 102 may be configured to initiate scanning of the eye 130 in response to receiving a command and/or instruction from the OCT controller 104. The OCT controller 104 may be configured to transmit a scan initiation command to the OCT scanner 102 in response to receiving an indication from a user, such as a surgeon to initiate scanning of the eye. The OCT controller 104 may be configured to receive the indication to initiate scanning of the eye via a user interface (e.g., a graphical user interface (GUI)) and/or an input device (not shown). Input devices may be communicatively coupled to and/or incorporated in the imaging system 106. Examples of input devices include, but are not limited to, a key pad, a keyboard, a touch screen device configured to receive touch inputs, and the like.

In some implementations, the indication from the user may provide information related to depth and/or location of the eye for scanning, and the OCT controller 104 may be configured to provide the received eye depth and/or location related information to the OCT scanner 102. For example, an indication received by the OCT controller 104 may indicate a full eye OCT scan, and the OCT controller 104 may transmit an instruction to the OCT scanner 102 that indicates a full eye OCT scan. Similarly, an indication received by the OCT controller 104 may indicate an OCT scan of the retina of the eye, and the OCT controller 104 may transmit an instruction to the OCT scanner 102 that indicates an OCT scan of the retina of the eye.

The OCT controller 104 may be communicatively coupled to the OCT scanner 102 via one or more electrical and/or communication interfaces. In some implementations, the one or more electrical and/or communication interfaces may be configured to transmit data (e.g., scan data generated by the OCT scanner 102) from the OCT scanner 102 at a high transmission rate such that the OCT controller 104 may receive the data in real-time or near real-time from the OCT scanner 102.

The OCT controller 104 may be configured to generate one or more OCT images based on the received generated scan data from the OCT scanner 102. For example, the OCT controller 104 may be configured to generate a 2D image or a B-scan image based on the generated 2D scan data of a line scan. Similarly, the OCT controller 104 may be configured to generate a 3D image or a C-scan based on the generated 3D scan data of an area scan. The OCT controller 104 may be configured to perform image generation and/or image processing in real-time and/or near real-time.

The OCT controller 104 may be configured with one or more tissue detection and/or auto-segmentation algorithms to detect and/or auto-segment one or more tissue layers of the eye in the generated OCT images. Examples of tissue of an eye that the OCT controller 104 may be configured to detect and/or auto-segment include, but are not limited to, anterior surface of the cornea, retina, cornea, iris, pupil, anterior and posterior surface plus the position of the lens, internal limiting membrane (ILM), and the like. The OCT controller 104 may be configured to apply one or more tissue detection and/or auto-segmentation algorithms on the received scan data from the OCT scanner 102 and/or the generated OCT images to detect and/or auto-segment one or more tissues of the scanned eye.

The OCT controller 104 may be configured to determine a set of positions in a three dimensional (3D) coordinate system for each detected tissue of the eye based on the position data of the galvanometer scanners received from the absolute and the incremental encoders coupled to the galvanometer scanners and the scan data received when the position data is received. For example, during the OCT scan, the OCT controller 104 may receive position data of the galvanometer scanners and scan data including data related to the surface of the retina (e.g., ILM), and the OCT controller 104 may detect the surface of the retina based on the received scan data and determine a position of the surface of the retina in the 3D coordinate system based on the position data received when the scan data including the data related to surface of the retina is received.

In some implementations, the OCT controller 104 may be configured to determine a position of a detected tissue in the 3D coordinate system based on the mechanical angles of the galvanometer scanners when the scan data corresponding to the detected tissue is captured and/or generated by the OCT scanner 102. In some implementations, the OCT controller 104 may be configured with a set of rules and/or instructions to translate mechanical angles of the galvanometer scanners to positions in 3D coordinate system. For example, for the initial received position data of the galvanometer scanners, the OCT controller 104 may associate that data with an initial coordinate or a central coordinate of the 3D coordinate system, and for the second received position data of the galvanometer scanners, the OCT controller 104 may associate that data with a second coordinate of the coordinate system. In such implementations, the OCT controller 104 may determine the second coordinate based on the difference between the initially received position data of the galvanometer scanners and the second received position data of the galvanometer scanners (e.g., difference between the mechanical angles of the initial received position data and the mechanical angles of the second received position data).

The coordinate system in which the OCT controller 104 determines the set of positions for each detected tissue may be referred to herein as the coordinate system of the OCT system 100. An example of a position in the coordinate system of the OCT system 100 of a detected tissue, such as a target tissue on surface of the retina (e.g., ILM) in the eye 130, may be determined by the OCT controller 104 to be at a coordinate (−3, −2, −5) of 3D coordinate system, where the first value (−3) is a value on an x-axis, the second value (−2) is a value of y-axis, and the third value (−5) is a value on a z-axis of the 3D coordinate system.

In some implementations, the values of the positions determined by the OCT controller 104 may indicate offsets from a central or an initial coordinate of the 3D coordinate system. In some implementations, the OCT controller 104 may be configured to set a central coordinate of the 3D coordinate system as a location (e.g., center point) on the surface of the eye 130, such that all other positions of the 3D coordinate system represent offsets from the central coordinate, and the first received scan data may correspond to that location (e.g., center point) on the surface of the eye 130. The OCT controller 104 may be configured to store the position data of the detected tissues of the eye in a data storage unit of the OCT system 100.

The OCT controller 104 may be communicatively coupled to display 108 and external display 110. The OCT controller 104 may cause the generated OCT images to be displayed on the display 108 and/or the external display 110. For example, the OCT controller 104 may transmit the generated OCT images to the display 108 and/or the external display 110. In some implementations, the OCT images may be displayed as en face OCT images by the display 108 and/or the external display 110. In some implementations, the OCT images may be displayed as semi-transparent OCT images with the one or more auto-segmented tissues (e.g., on the surface of the retina, and the like) may be displayed as a dot or wireframe array.

In some implementations, the OCT controller 104 may be communicatively coupled to one or more image capture devices (not shown separately), and the OCT controller 104 may be configured to receive optical images from the one or more image capture devices that are communicatively coupled to the OCT controller 104. The OCT controller 104 may be configured to overlay the generated OCT images on the received optical images. In some implementations, the OCT controller 104 may receive three dimensional optical images. The OCT controller 104 may be configured to overlay OCT images (e.g., en face OCT images) on 3D optical images.

Examples of overlaying OCT images on optical images are disclosed in U.S. Pat. No. 10,398,307, entitled CURVATURE OF FIELD TRANSFORMATION OF OCT IMAGES DURING VITREORETINAL SURGERY, the entire disclosure of which is hereby incorporated by reference herein. Examples of generating en face OCT images are disclosed in U.S. Pat. No. 10,064,549, entitled BINOCULAR EN FACE OPTICAL COHERENCE TOMOGRAPHY IMAGING, the entire disclosure of which is hereby incorporated by reference herein. Examples of generating OCT images during vitreoretinal surgery are disclosed in U.S. Pat. No. 9,649,021, entitled RESOLUTION ENHANCEMENT OF OCT IMAGES DURING VITREORETINAL SURGERY, the entire disclosure of which is hereby incorporated by reference herein. Examples of generating OCT images during vitreoretinal surgery are disclosed in U.S. Pat. No. 10,013,749, entitled RESOLUTION ENHANCEMENT OF OCT IMAGES DURING VITREORETINAL SURGERY, the entire disclosure of which is hereby incorporated by reference herein. Examples of en face or 3D volumetric OCT imaging during ophthalmic surgery are disclosed in U.S. Pat. No. 10,285,584, entitled SUBTRACTIVE EN FACE OPTICAL COHERENCE TOMOGRAPHY IMAGING.

The display 108 and the external display 110 may be part of an ophthalmic visualization system that provides a platform for digitally assisted ophthalmic procedures, such as NGENUITY 3D Visualization system of Alcon Laboratories Inc. In some implementations, display 108 may be a display for the user (e.g., surgeon, and the like) and the display 110 may be a stand-alone monitor for viewing by various personnel during the ophthalmic procedure.

In some implementations, the display 108 and/or 110 may be implemented as a 3D visualization system, a touchscreen device, a liquid crystal display screen, a computer monitor, a television, a tablet, augmented glasses, viewing glasses, and the like. The display 108 and/or 110 may be configured to be in compliance with one or more display standards, such as video graphics array (VGA), extended graphics array (XGA), digital visual interface (DVI), high-definition multimedia interface (HDMI), and the like. In certain implementations, display 108 and/or 110 may be organic light emitting diode (OLED) displays used in the NGENUITY 3D Visualization system of Alcon Laboratories Inc.

In some implementations, the OCT controller 104 may be configured to transmit the received scan data from the OCT scanner 102 to the imaging system 106. The imaging system 106 may be configured to receive the generated scan data and process the scan data to generate one or more OCT images for display to a user (e.g., a surgeon, a clinician, and the like). The imaging system 106 may be configured with one or more tissue detection and/or auto-segmentation algorithms to detect and/or auto-segment one or more tissue layers of the eye in the generated OCT images. The imaging system 106 may be configured to support three dimensional (3D) visualization of the images. The imaging system 106 may be configured to capture and/or generate one or more optical images of the eye 130 and the imaging system 106 may overlay the generated one or more OCT images on the captured and/or generated one or more optical images.

For example, the imaging system 106 may transmit the optical images overlaid with OCT images to the display 108 to cause the images to be displayed to the user. In some implementations, the imaging system 106 may be configured to provide the optical images overlaid with OCT images, generated OCT images, and/or the auto-segmented tissues of the OCT images to the OCT controller 104. For example, the imaging system 106 may transmit the optical images overlaid with OCT images to the OCT controller 104, and the OCT controller 104 may be configured to transmit the digital optical images overlaid with OCT images to the external display 110 for displaying the digital optical images overlaid with OCT images to the user and/or other personnel.

As described above, the robotic device 120 may be communicatively coupled to the OCT system 100. The robotic device 120 includes robotic device controller 122, and a surgical instrument 124. The robotic device controller 122 may be configured to receive inputs from the OCT controller 104. Examples of inputs from the OCT controller 104 may include, but are not limited to, instructions to move the surgical instrument to a position in a 3D coordinate system of the robotic device 120. The 3D coordinate system of the robotic device 120 may be different from the 3D coordinate system in which the positions of the tissues of the eye are determined (e.g., the 3D coordinate system of the OCT system). Additional details of transforming from the 3D coordinate system of positions of the tissues to the 3D coordinate system of the robotic device 120 are described below. In some implementations, the robotic device 120 may be configured to move with six degrees of freedom (6-DOF).

The robotic device 120 may be configured to be interacted with by a user (e.g., a surgeon) via an interface to move the robotic device 120, and the robotic device controller 122 may be configured to receive inputs from the user via the interface. For example, the robotic device 120 may be communicatively coupled to a surgeon console, and a user, such as a surgeon, may interact with a six degrees of freedom (6-DOF) haptic interface of the surgeon console to move the surgical instrument 124 of the robotic device 120 to a desired position. The user (e.g., surgeon) may position uses the haptic interface to position a surgical tool near the target tissue in the eye 130. The robotic device controller 122 may be configured to receive the movements of the 6-DOF haptic interface of the surgeon console from the surgeon console and determine a position in the 3D coordinate system of the robotic device to move the surgical instrument 124, and may cause the surgical instrument 124 to the user's desired position.

For example, after viewing a desired tissue of the eye 130 displayed on OCT images on the display 108 and/or 110, a user (e.g., a surgeon, and the like) may interact with the robotic device 120 to move the surgical instrument to a position near the eye 130. For example, the user may cause the surgical instrument to be positioned near the target tissue in the eye. The robotic device controller 122 may transmit the position of the surgical instrument to the OCT controller 104.

The user may select a tissue on the display 108 and/or 110 and indicate a task that the user desires the robotic device 120 to perform. For example, the user may touch the a target location on the surface of the retina displayed in the OCT image overlaid optical image on the display 108 and/or 110 to select the target location on the surface of the retina as the target tissue on which to operate, and the user may also select a task such as removal of a membrane (e.g., ILM) for the robotic device 120 to perform. In some implementations, the user may virtually draw a motion of the task and/or operation that the user desires the robotic device 120 to perform. For example, the user may virtually draw a circular motion on a display 108 and/or 110 that is displaying a certain location on the surface of the retina to indicate a removal of a membrane (e.g., ILM or epiretinal membrane) from such certain location.

The display 108 and/or 110 may be configured to transmit the task and/or operation received from the user to the OCT controller 104. The OCT controller 104 may be configured to transmit the received task and/or operation from the user to the robotic device controller 122. The robotic device controller 122 may be configured to transmit a position of the surgical instrument 124 to the OCT controller 104. In some implementations, the robotic device controller 122 may be configured to transmit the position of the surgical instrument 124 to the OCT controller 104 in response to receiving the task and/or operation from the user. For example, in response to receiving the task and/or operation information from the user via the OCT controller 104, the robotic device controller 122 may transmit the position information of the surgical instrument 124.

The robotic device controller 122 may transmit the position information of the surgical instrument 124 in the coordinate system of the robotic device 120. The OCT controller 104 may be configured to transform the positions and/or coordinates in the 3D coordinate system of the robotic device 120 to the positions and/or coordinates in the 3D coordinate system in which the OCT controller 104 determined the positions of the detected tissues (e.g., the 3D coordinate system of the OCT system 100, and vice-versa. The OCT controller 104 may be configured to apply one or more transformation techniques to transform the positions from one coordinate system to another coordinate system. For example, the OCT controller 104 may be configured to apply a Jacobean transform to the coordinates in one coordinate system in order to transform them into coordinates in the other coordinate system.

In some implementations, the OCT controller 104 may be configured with a mapping between coordinates of coordinate system in which the OCT controller 104 determines the positions of the tissues and the coordinate system of the robotic device 120. Based on the mapping, the OCT controller 104 may be configured to transform the coordinates in a first coordinate system to coordinates in a second coordinate system. For example, for a position (−3, −2, −5) in one 3D coordinate system, the mapping may indicate that the position transforms to (2, 1, 4) in the other 3D coordinate system.

Based on the received selection of the tissue, the OCT controller 104 may identify the position of the tissue in the 3D coordinate system of OCT system 100. The OCT controller may utilize a transformation technique and/or the mapping between coordinate systems of the OCT system 100 and the robotic device 120 to determine the position of the tissue in the 3D coordinate system of the robotic device 120. For example, if the user selects a target tissue (e.g., certain location on the surface of the retina or another location in the eye) and the position of the target tissue in the 3D coordinate system of the OCT system 100 is (−3, −2, −5), then the OCT controller 104 may determine the position of the target tissue in the 3D coordinate system of robotic device 120 by utilizing a transformation technique and/or a mapping between the two 3D coordinate systems to determine the position of the target tissue in the eye 130 in the 3D coordinate system of the robotic device 120. In certain embodiments, a rigid, precise mechanical mounting of the OCT system 100 and a base of the robot device 120 is necessary or at least advantageous.

The OCT controller 104 may transmit the position determined in the 3D coordinate system of the robotic device 120 of the user selected target tissue to the robotic device 120 and cause the robotic device 120 to move the surgical instrument to that position. For example, the OCT controller 104 may transmit the position of the target tissue (e.g., a location on the surface of the retina) in the 3D coordinate system of the robotic device 120 to the robotic device controller 122, and, in response, the robotic device controller 122 may cause the surgical instrument to be moved to the position received from the OCT controller 104.

After the surgical instrument is moved to the position of the user selected tissue, the robotic device 120 may be configured to perform the task selected by the user. For example, if the user selected the task of removing a membrane from the target tissue, then the robotic device controller 122 may cause the surgical instrument to remove the membrane. Similarly, if the user virtually draws a motion or task to perform on the tissue, the OCT controller 104 may transmit information related to that motion or task to the robotic device controller 122, and the robotic device controller 122 may cause the surgical instrument to perform the motion or task.

Figure 2:
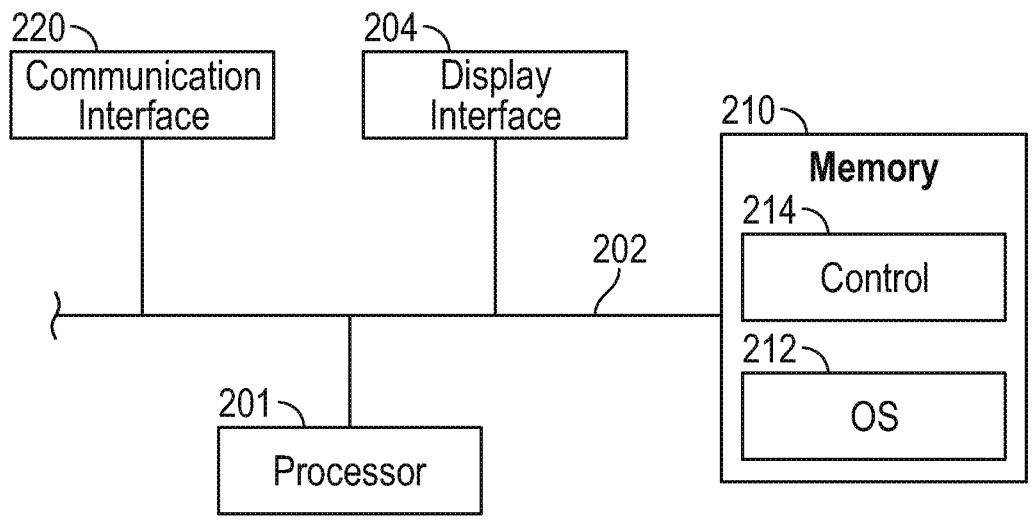
FIG. 2 illustrates a block diagram of selected components of an OCT controller, in accordance with certain embodiments of the present disclosure.

FIG. 2 illustrates a block diagram of selected components of an implementation of an OCT controller, such as the OCT controller 104 as described above in reference with FIG. 1. As shown in FIG. 2, OCT controller 104 includes processor 201, bus 202, display interface 204, memory 210, and communication interface 220.

The processor 201 may be communicatively coupled to memory 210, display interface 204, and communication interface 220 via bus 202. The OCT controller 104 may be configured to interface with various external components (e.g., OCT scanner 102, imaging system 106, display 108, external display 110, and the like) of an OCT system (e.g., OCT system 100) via processor 201 and communication interface 220. In some implementations, communication interface 220 may be configured to enable OCT controller 104 to connect to a network (not shown). In some implementations, the OCT controller 104 may be connected to one or more displays, such as display 108, external display 110, and the like, via display interface 204.

The memory 210 may include persistent, volatile, fixed, removable, magnetic, and/or semiconductor media. The memory 210 may be configured to store one or more machine-readable commands, instructions, data, and/or the like. In some implementations, as shown in FIG. 2, the memory 210 may include one or more sets and/or sequences of instructions, such as an operating system 212, a scanning control application 214, and the like. Examples of operating system 212 may include, but are not limited to, real-time operating systems, such as ThreadX provided by Express Logic, VxWorks provided by Wind River, Integrity provided by Green Hills, QNX, etc.

The scanning control application 214 may be configured to perform OCT controller operations as described herein including, but not limited to, operations related to initiation of scanning of the eye, generation of OCT images, OCT image processing, receiving position data of the galvanometer scanners from the absolute encoders, receiving scan data, determining positions of one or more tissues of the eye in a first 3D coordinate system (e.g., the 3D coordinate system of the OCT system 100), determining a position in a second 3D coordinate system (e.g., the 3D coordinate system of the robotic device 120) based on the positions of the tissues in the first 3D coordinate system, causing a communicatively coupled robotic device (e.g., robotic device 120) to move a surgical instrument to the position in the second 3D coordinate system, and the like.

Figure 3:
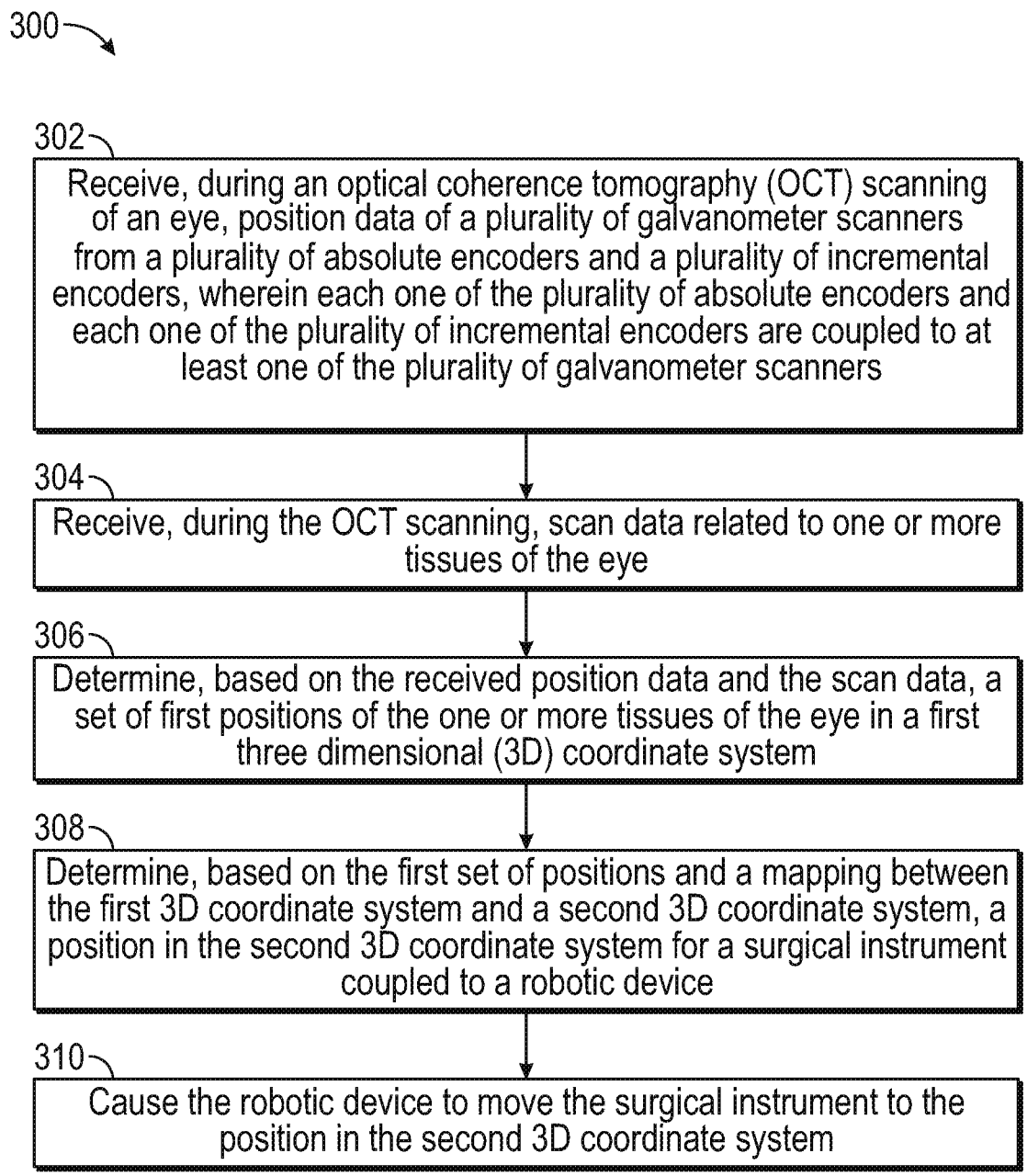
FIG. 3 illustrates a flow chart of an example method for guiding a robotic device for an ophthalmic procedure, in accordance with certain embodiments of the present disclosure.

FIG. 3 illustrates a flow chart of an example method for guiding a robotic device for an ophthalmic procedure, in accordance with certain embodiments of the present disclosure. The operations 300 may be performed, for example, by an OCT controller (e.g., the OCT controller 104 of OCT system 100). The operations 300 may be implemented as software components that are executed and run on one or more processors (e.g., processor 201).

The operations 300 may begin at 302, where the OCT controller 104 receives, during an OCT scanning of an eye, position data of the plurality of galvanometer scanners from the plurality of absolute encoders and a plurality of incremental encoders, wherein each absolute encoder of the plurality of absolute encoders and each incremental encoder of the plurality of incremental encoders are coupled to at least one galvanometer scanner of the plurality of galvanometer scanners.

At 304, the OCT controller 104, receives, during the OCT scanning, scan data related to one or more tissues of the eye. At 306, the OCT controller 104, determines, based on the received position data and the scan data, a set of first positions of the one or more tissues of the eye in a first three-dimensional (3D) coordinate system.

At 308, the OCT controller 104, determines, based on the first set of positions and a mapping between the first 3D coordinate system and a second 3D coordinate system, a position in the second 3D coordinate system for a surgical instrument coupled to a robotic device. At 310, the OCT controller 104, causes the robotic device to move the surgical instrument to the position in the second 3D coordinate system.

In some implementations, the OCT controller 104, initiates the OCT scanning of the eye in response to receiving a message indicating initiation of the OCT scanning of the eye, and generates, based on the OCT scanning, a real-time 3D image of the eye in the first 3D coordinate system. In some implementations, to determine the position in the second 3D coordinate system, the OCT controller 104, receives (e.g., from a user) a selection of a location in the real-time 3D image corresponding to a first tissue of the one or more tissues of the eye, and maps, based on the first set of positions and the mapping between the first 3D coordinate system and a second 3D coordinate system, the location to the determined position in the second 3D coordinate systems.

In some implementations, the OCT controller 104, provides the real-time 3D image of the eye for display to a user. In some implementations, at least one absolute encoder of the plurality of absolute encoders is a sine-cosine encoder. In some implementations, at least one absolute encoder of the plurality of absolute encoders is a holographic encoder. In some implementations, at least one galvanometer scanner of the plurality of galvanometer scanners is configured to scan in a first direction and at least one other galvanometer scanner of the plurality of galvanometer scanners is configured to scan in a second direction. In some implementations, the first direction is perpendicular to the second direction. In some implementations, at least one galvanometer scanner of the plurality of galvanometer scanners is a moving-magnet galvanometer scanner.

The methods and apparatus described above provide novel systems and methods for guiding a robotic device for an ophthalmic procedure using data generated and/or captured during an OCT scan of an eye. For example, the described systems and methods determine positions of detected tissues in a coordinate system based on position data of galvanometer scanners received from absolute and incremental encoders coupled to the galvanometer scanners, which improve the accuracy of determining positions of various detected tissues of an eye in a coordinate space and improve the accuracy of moving robot-driven surgical instruments to a user selected tissue for an ophthalmic procedure.

While the foregoing is directed to embodiments of the present disclosure, other and further embodiments of the disclosure may be devised without departing from the basic scope thereof, and the scope thereof is determined by the claims that follow.

Example Embodiments

Embodiment 1: A method comprising: receiving, during an optical coherence tomography (OCT) scanning of an eye, position data of a plurality of galvanometer scanners from a plurality of absolute encoders and a plurality of incremental encoders, wherein each one of the plurality of absolute encoders and each one of the plurality of incremental encoders are coupled to at least one of the plurality of galvanometer scanners; receiving, during the OCT scanning, scan data related to one or more tissues of the eye; determining, based on the received position data and the scan data, a set of first positions of the one or more tissues of the eye in a first three-dimensional (3D) coordinate system; determining, based on the first set of positions and a mapping between the first 3D coordinate system and a second 3D coordinate system, a position in the second 3D coordinate system for a surgical instrument coupled to a robotic device; and causing the robotic device to move the surgical instrument to the position in the second 3D coordinate system.

The method of embodiment 1, wherein at least one of the plurality of galvanometer scanners is configured to scan in a first direction and wherein at least another one of the plurality of galvanometer scanners is configured to scan in a second direction.

The method of embodiment 1, wherein the first direction is perpendicular to the second direction.

The method of embodiment 1, wherein at least one galvanometer scanner of the plurality of galvanometer scanners is a moving-magnet galvanometer scanner.

The method of embodiment 1, wherein at least one galvanometer scanner of the plurality of galvanometer scanners is an optical galvanometer scanner.

The method of embodiment 1, wherein the plurality of absolute encoders and the plurality of incremental encoders are integrated into a single device.

What is claimed is:

1. An optical coherence tomography (OCT) system, comprising:
   a plurality of galvanometer scanners;
   a plurality of absolute encoders and a plurality of incremental encoders, each one of the plurality of absolute encoders and each one of the plurality of incremental encoders coupled to at least one of the plurality of galvanometer scanners; and
   a controller coupled to the plurality of absolute encoders and the plurality of incremental encoders, the controller comprising:
      a processor, and
      a memory coupled to the processor and having instructions stored thereon, which when executed by the processor, causes the controller to:
         receive, during an optical coherence tomography (OCT) scanning of an eye, position data of the plurality of galvanometer scanners from the plurality of absolute encoders and the plurality of incremental encoders coupled to corresponding galvanometer scanners of the plurality of galvanometer scanners;
         receive, during the OCT scanning, scan data related to one or more tissues of the eye;
         determine, based on the received position data and the scan data, a set of first positions of the one or more tissues of the eye in a first three-dimensional (3D) coordinate system;
         determine, based on the first set of positions and a mapping between the first 3D coordinate system and a second 3D coordinate system, a position in the second 3D coordinate system for a surgical instrument coupled to a robotic device; and
         cause the robotic device to move the surgical instrument to the position in the second 3D coordinate system.

2. The OCT system of claim 1, wherein the processor further causes the controller to:
   initiate the OCT scanning of the eye in response to receiving a message indicating initiation of the OCT scanning of the eye; and
   generate, based on the OCT scanning, a real-time 3D image of the eye in the first 3D coordinate system.

3. The OCT system of claim 2, wherein to determine the position comprises to:
   receive a selection of a location in the real-time 3D image corresponding to a first tissue of the one or more tissues of the eye; and
   map, based on the first set of positions and the mapping between the first 3D coordinate system and a second 3D coordinate system, the location to the determined position in the second 3D coordinate systems.

4. The OCT system of claim 2, wherein the processor further causes the controller to:
   provide the real-time 3D image of the eye for display to a user.

5. The OCT system of claim 1, wherein at least one absolute encoder of the plurality of absolute encoders is a sine-cosine encoder.

6. The OCT system of claim 1, wherein at least one absolute encoder of the plurality of absolute encoders is a holographic encoder.

7. The OCT system of claim 1, wherein at least one galvanometer scanner of the plurality of galvanometer scanners is configured to scan in a first direction and wherein at least one other galvanometer scanner of the plurality of galvanometer scanners is configured to scan in a second direction.

8. The OCT system of claim 7, wherein the first direction is perpendicular to the second direction.

9. The OCT system of claim 1, wherein at least one galvanometer scanner of the plurality of galvanometer scanners is a moving-magnet galvanometer scanner.

10. A method of guiding a robotic device, comprising:
    receiving, during an optical coherence tomography (OCT) scanning of an eye, position data of a plurality of galvanometer scanners from a plurality of absolute encoders and a plurality of incremental encoders coupled to corresponding galvanometer scanners of the plurality of galvanometer scanners, each one of the plurality of absolute encoders and each one of the plurality of incremental encoders coupled to at least one of the plurality of galvanometer scanners;
    receiving, during the OCT scanning, scan data related to one or more tissues of the eye;
    determining, based on the received position data and the scan data, a set of first positions of the one or more tissues of the eye in a first three-dimensional (3D) coordinate system;
    determining, based on the first set of positions and a mapping between the first 3D coordinate system and a second 3D coordinate system, a position in the second 3D coordinate system for a surgical instrument coupled to the robotic device; and
    causing the robotic device to move the surgical instrument to the position in the second 3D coordinate system.

11. The method of claim 10, further comprising:
    initiating the OCT scanning of the eye in response to receiving a message indicating initiation of the OCT scanning of the eye; and
    generating, based on the OCT scanning, a real-time 3D image of the eye in the first coordinate system.

12. The method of claim 11, wherein determining the position further comprises:

receiving a selection of a location in the real-time 3D image corresponding to a first tissue of the one or more tissues of the eye; and mapping, based on the first set of positions and the mapping between the first 3D coordinate system and a second 3D coordinate system, the location to the determined position in the second 3D coordinate systems.

13. The method of claim 11, further comprising:

providing the real-time 3D image of the eye for display to a user.

14. The method of claim 10, wherein at least one absolute encoder of the plurality of absolute encoders is a sine-cosine encoder.

15. The method of claim 10, wherein at least one absolute encoder of the plurality of absolute encoders is a holographic encoder.

* * * * *